United States Patent [19]

Hancock et al.

[11] Patent Number: 6,164,137
[45] Date of Patent: Dec. 26, 2000

[54] ELECTROMAGNETIC ACOUSTIC TRANSDUCER (EMAT) INSPECTION OF TUBES FOR SURFACE DEFECTS

[75] Inventors: Jimmy W. Hancock; Daniel T. MacLauchlan, both of Lynchburg, Va.

[73] Assignee: McDermott Technology, Inc., New Orleans, La.

[21] Appl. No.: 09/243,592

[22] Filed: Feb. 3, 1999

[51] Int. Cl.[7] .......................... G01N 29/08; G01N 29/28
[52] U.S. Cl. ................... 73/643; 73/622; 73/598; 376/249
[58] Field of Search ........................ 73/643, 620, 622, 73/597, 598; 376/252, 249

[56] References Cited

U.S. PATENT DOCUMENTS

| | | | |
|---|---|---|---|
| 4,092,868 | 6/1978 | Thompson et al. | 73/638 |
| 4,372,163 | 2/1983 | Tittmann et al. | 73/602 |
| 4,843,884 | 7/1989 | House et al. | 73/622 |
| 5,085,082 | 2/1992 | Cantor et al. | 73/622 |
| 5,113,697 | 5/1992 | Schlawne | 73/602 |
| 5,679,898 | 10/1997 | Sclawne et al. | 73/622 |
| 5,763,786 | 6/1998 | Camplin et al. | 73/643 |
| 5,767,408 | 6/1998 | Lindgren et al. | 73/597 |

*Primary Examiner*—Hezron Williams
*Assistant Examiner*—Rose M. Miller
*Attorney, Agent, or Firm*—R. J. Edwards; Eric Marich; R. C. Baraona

[57] ABSTRACT

An EMAT testing device for nondestructively testing tubes for surface defects and displaying the results has a EMAT transmitter arranged collinear with a pair of EMAT receivers. The EMAT receivers each receive a pair of oppositely propagating circumferential acoustic surface waves from the transmitter at different times and the relative amplitudes of the received waves are compared to located defects adjacent the receivers in the tube.

10 Claims, 1 Drawing Sheet

ELECTROMAGNETIC ACOUSTIC TRANSDUCER (EMAT) INSPECTION OF TUBES FOR SURFACE DEFECTS

FIELD AND BACKGROUND OF THE INVENTION

The present invention relates generally to the field of nondestructive testing of components and in particular to a new and useful method and apparatus for nondestructively testing tubes, such as are used in industrial boilers, for surface defects using electromagnetic acoustic transducer technology.

Electromagnetic acoustic transducers (EMATs) are known for use in testing materials for defects. In known systems, a signal generator creates an acoustic wave which propagates through a test material and either the original signal or a reflection is received by a single sensor having a coil for converting acoustic wave energy to an electrical current. EMATs are typically used on planar surfaces of a test material to detect both surface and sub-surface defects in the test material.

Tubes present a challenge for testing due to their curved surfaces. Tubes used in industrial boilers present a further challenge, as the space around and access to the tubes is typically very limited. These tubes must be as free of defects as possible, and coated with materials to resist corrosion and breakdown in the harsh environment of an industrial boiler.

Testing techniques such as conventional ultrasonic, eddy current, magnetic particle and dye penetrant testing all have limitations which prevent them from being used to perform high speed testing of 100% of the surface area of a tube. For example, ultrasonic testing requires a couplant material used with the sensor on the tube surface to ensure accurate signal pickup. Eddy current testing is susceptible to material variations and other properties within the material which can mask defects, or result in incorrect readings. Magnetic particle and dye penetrant testing each require a large amount of chemicals to coat the tubes and a long period of time to interpret results as well.

EMATs, by comparison, do not require couplants or chemicals, and since they rely on detection of the amplitude of acoustic signals which are converted to electrical signals, the testing may be done rapidly and the results displayed contemporaneously with the testing.

SUMMARY OF THE INVENTION

It is an object of the present invention to provide a rapid and efficient method and apparatus for detecting surface defects in tubes, particularly tubes used in industrial boilers.

It is a further object of the invention to provide a method and apparatus for quickly testing tubes for surface and displaying the test results rapidly.

Accordingly, an electromagnetic acoustic transducer tester for tubes is provided having a housing with a single transmitter and a pair of receivers arranged sequentially to fit circumferentially around a tube. Both receivers are arranged on one side of the transmitter. The transmitter generates a surface wave acoustic signal which propagates around the circumference of the tube in opposite directions. The two receivers each detect the two acoustic surface waves signals, unless a defect is present, in which case the received signal will be attenuated by the defect and will not be sufficient to generate an electrical signal in the receiver. The receivers convert the acoustic surface waves to electrical signals, which may be viewed on a display unit, thereby permitting simple and rapid viewing and analysis of the testing results.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
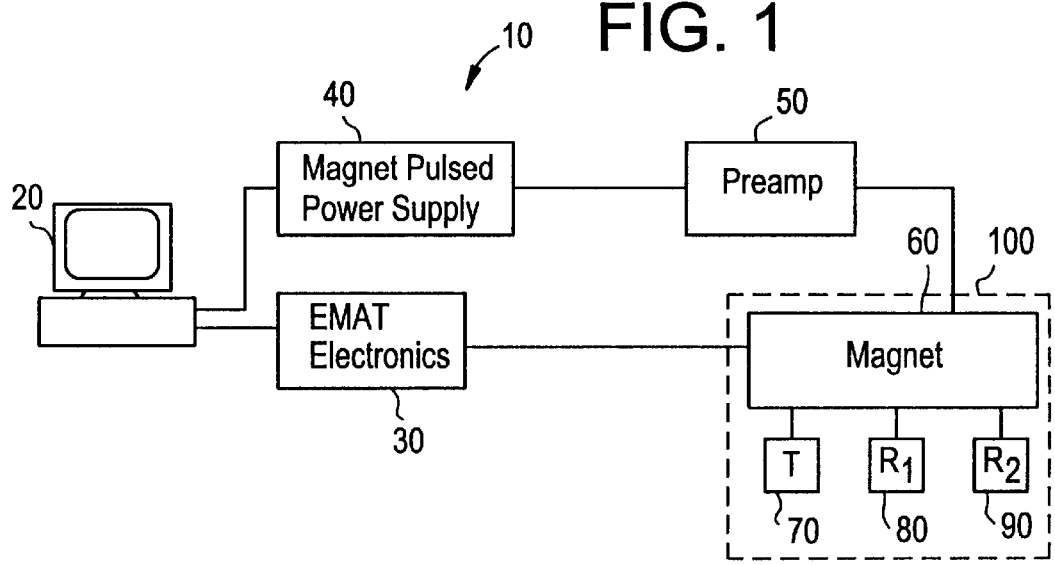
FIG. 1 is a schematic diagram of a testing device according to the invention.

Referring now to the drawings, in which like reference numerals are used to refer to the same or similar elements, FIG. 1 is a schematic diagram showing the components of an electromagnetic acoustic transducer testing device 10 which can be used to test a tube for defects. A computer 20 is used to control the testing and display test results for analysis. Any known type of computer having peripheral ports to connect to EMAT electronics 30 and magnet pulsed-power supply 40 may be used. A preamp 50 connects the pulsed-power supply 40 to magnet 60, transmitter 70 and receivers R1 80 and R2 90. EMAT electronics 30 are connected directly to the magnet 60 and transmitter 70 and receivers 80, 90.

The magnet 60, transmitter 70 and receivers R1 80 and R2 90 are contained in a sensor housing 100. Preferably, the receivers R1 80 and R2 90 are both located to the same side of transmitter 70 and arranged collinear, so that they may be mounted circumferentially on a tube in sequence.

The EMAT components 30, 40, 50, 60, 70, 80, 90 each function in a known manner used for EMAT testing. A signal is generated and sent to the coil of transmitter 70 to be transferred to and propagate through the test subject, in this case a tube. The original signal or reflections are received by the coils of each receiver R1 80 and R2 90 and converted to electrical signals which are modified as needed and displayed on computer 20. Computer 20 can also be optionally used to control the testing signal generation and to analyze the results displayed.

Figure 2:
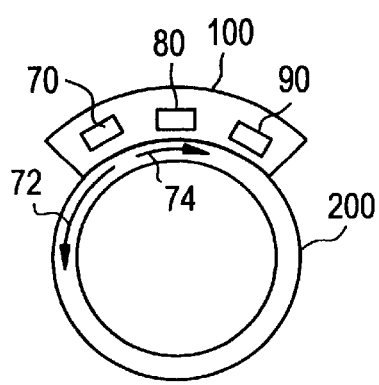
FIG. 2 is an end elevational view of a tube being tested by the device of FIG. 1.

The testing device 10 is used to determine if defects exist in a tube 200, such as shown in FIG. 2 by mounting the sensor housing 100 on the surface of the tube 200 and generating a signal in the transmitter 70. The transmitter creates two surface waves 72, 74 which propagate in opposite directions around the circumference of the tube 200. One wave 72 propagates in a counter-clockwise direction from the transmitter 70, the other wave 74 in a clockwise direction. The waves have substantially the same amplitude. Their amplitudes will not change in the absence of defects in the tube under one of the receivers R1 80 or R2 90.

Figure 3:
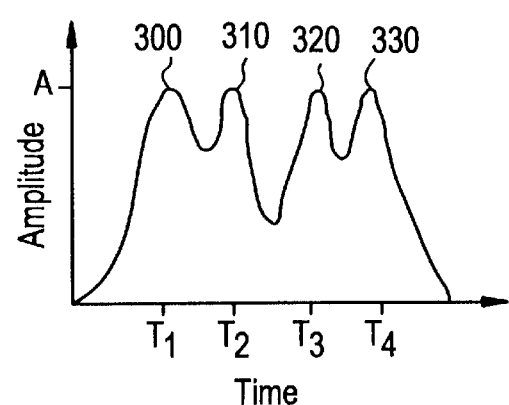
FIG. 3 is a graph showing the relative amplitudes of test signals received by the device used on the tube of FIG. 2.

Referring also to FIG. 3 for the timing of the signals received by the receivers R1 80 and R2 90, receiver R2 90 detects counter-clockwise wave 72 at a first time T1 and generates an electrical signal 300 proportionate to the acoustic signal amplitude. Then, at time T2, receiver R1 80 detects the wave 72 and also generates an electrical signal 310 proportionate to the acoustic signal and having nearly the same amplitude A as the first signal 300. The nearly identical amplitudes of each signal 300, 310 indicate that there are no defects in the tube 200.

The receiver R1 80 receives the clockwise wave 74 first after one circle around the tube 200 at time T3 and generates a third signal 320 also having amplitude A. Shortly thereafter at time T4, receiver R2 90 generates signal 330 having amplitude A.

Figure 4:
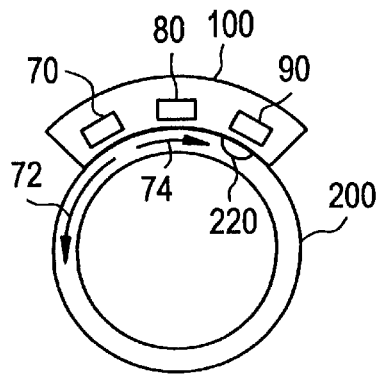
FIG. 4 is an end elevational view of another tube with a defect being tested by the device of FIG. 1.
Figure 5:
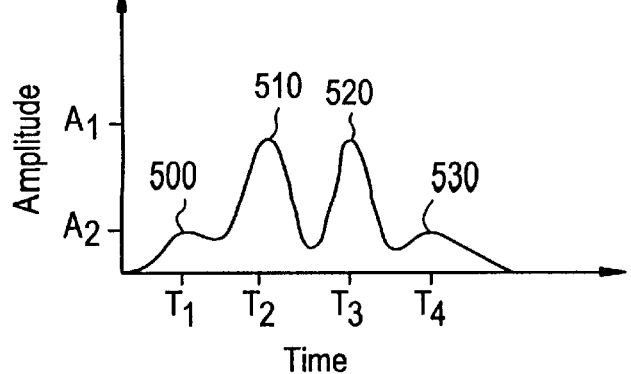
FIG. 5 is a graph showing the relative amplitudes of test signals received by the device used on the tube of FIG. 4.

In the case where a defect 220 is present under one of the receivers, R2 90 as shown in FIG. 4, the amplitudes of the signals 500, 510, 520, 530 (shown in FIG. 5) generated by the receivers R1 80 and R2 90 differ. Signals 500 and 530 generated by receiver R2 90 at times T1 and T4 have a lower amplitude A2 due to the presence of defect 220 under the receiver R2 90. The amplitude A1 of signals 510 and 520 from receiver R1 80 is similar to those generated by the receivers 80, 90 when no defect is present as the signal transmitted by transmitter 70 is not attenuated. The lower amplitude A2 of signals 500, 530 can also be caused by a lift-off effect of the defect 220 on the receiver R2 90. Since the receiver R2 90 is not capable of making good contact with the tube 200 because of the presence of defect 220, the received amplitude of the acoustic signal is lower, and so the proportionate electrical signal generated by the receiver R2 90 is likewise lower.

Thus, a tube 200 may be rapidly tested for defects by moving the sensor housing 100 circumferentially and longitudinally around the tube and transmitting oppositely propagating waves 72, 74, while reviewing the relative amplitudes of the received signals from the receivers R1 80 and R2 90.

While a specific embodiment of the invention has been shown and described in detail to illustrate the application of the principles of the invention, it will be understood that the invention may be embodied otherwise without departing from such principles.

We claim:

1. An EMAT testing device for nondestructively detecting defects in the surface of a tube using acoustic surface waves, the device comprising:

transmitter means for generating and transmitting a pair of acoustic surface wave signals in opposite directions around a circumference of the tube;

first receiving means for receiving each of the pair of acoustic surface waves signals at first and second times and converting the received acoustic surface waves signals to a pair of electronic signals having amplitudes proportionate to the acoustic surface wave signal amplitudes received at the first and second times;

second receiving means for receiving each of the pair of acoustic surface wave signals at third and fourth times and converting the received acoustic surface wave signals to a second pair of electronic signals having amplitudes proportionate to the acoustic surface wave signal amplitudes received at the third and fourth times, and computing means for comparing the amplitudes of the first pair of electronic signals to the amplitudes of the second pair of electronic signals and for determining the presence of defects in the surface of the tube from the comparison of the amplitudes of the two pair of electronic signals, whereby when no defects are present in the tube, the amplitudes of the two pairs of electronic signals are substantially the same, and when a defect is present adjacent one of the first receiving means and second receiving means, the corresponding amplitude of the electronic signal from the receiving means adjacent the defect is lower than the amplitude of the corresponding electronic signal from the other receiving means.

2. The EMAT testing device according to claim 1, further comprising display means for displaying the amplitudes of the two pairs of electronic signals.

3. The EMAT testing device according to claim 2, further comprising a sensor housing containing the transmitter means, the first receiving means and the second receiving means.

4. The EMAT testing device according to claim 3, wherein the transmitter means, first receiving means and second receiving means are arranged collinear in the housing.

5. The EMAT testing device according to claim 1, further comprising a sensor housing containing the transmitter means, the first receiving means and the second receiving means.

6. The EMAT testing device according to claim 5, wherein the transmitter means, first receiving means and second receiving means are arranged collinear in the housing.

7. The EMAT testing device according to claim 6, wherein the first receiving means and second receiving means are both located to the same side of the transmitting means.

8. The EMAT testing device according to claim 1, wherein the transmitter means comprises an EMAT transmitter, the first receiving means comprises a first EMAT receiver, and the second receiving means comprises a second EMAT receiver.

9. The EMAT testing device according to claim 8, further comprising display means for displaying the amplitudes of the two pairs of electronic signals.

10. The EMAT testing device according to claim 8, further comprising a sensor housing containing each of the EMAT transmitter, the first EMAT receiver and the second EMAT receiver.

* * * * *